(12) United States Patent
Bhat

(10) Patent No.: US 12,053,477 B2
(45) Date of Patent: Aug. 6, 2024

(54) METHODS FOR TREATING PULMONARY FIBROSIS

(71) Applicant: Reviva Pharmaceuticals, Inc., Cupertino, CA (US)

(72) Inventor: Laxminarayan Bhat, Cupertino, CA (US)

(73) Assignee: REVIVA PHARMACEUTICALS, INC., Cupertino, CA (US)

( * ) Notice: Subject to any disclaimer, the term of this patent is extended or adjusted under 35 U.S.C. 154(b) by 0 days.

(21) Appl. No.: 17/656,743

(22) Filed: Mar. 28, 2022

(65) Prior Publication Data

US 2023/0061592 A1   Mar. 2, 2023

Related U.S. Application Data

(63) Continuation of application No. 17/143,872, filed on Jan. 7, 2021, now abandoned, which is a continuation of application No. 16/913,414, filed on Jun. 26, 2020, now abandoned, which is a continuation of application No. PCT/US2018/067999, filed on Dec. 28, 2018.

(60) Provisional application No. 62/611,501, filed on Dec. 28, 2017.

(51) Int. Cl.
*A61K 31/538* (2006.01)
*A61K 9/00* (2006.01)
*A61P 11/00* (2006.01)

(52) U.S. Cl.
CPC .......... *A61K 31/538* (2013.01); *A61K 9/0053* (2013.01); *A61P 11/00* (2018.01)

(58) Field of Classification Search
CPC ..... A61K 31/538; A61K 9/0053; A61P 11/00; C07D 265/36
See application file for complete search history.

(56) References Cited

U.S. PATENT DOCUMENTS

| 10,441,590 B2 | 10/2019 | Bhat et al. |
| 2011/0171193 A1 | 7/2011 | Zhao et al. |
| 2013/0131081 A1 | 5/2013 | Moon et al. |

FOREIGN PATENT DOCUMENTS

| WO | 9825617 A1 | 6/1998 |
| WO | 2010099502 A1 | 9/2010 |
| WO | 2016115039 A1 | 7/2016 |
| WO | WO-2016115039 A1 * | 7/2016 | .......... A61K 31/538 |
| WO | 2014058000 A1 | 4/2017 |

OTHER PUBLICATIONS

Seeger et. al., J. Amer. College Cardiol., vol. 62, pp. D109-D116, publ. 2013 (Year: 2013).*
Field et. al., PLoS One, vol. 7(3), pp. 1-11, publ. Mar. 19, 2012 (Year: 2012).*
Papaioannou et. al., Respiratory Med., vol. 117, pp. 14-26, publ. 2016 (Year: 2016).*
Habeeb Ba Aqeel et. al., Annals of Translational Med., vol. 4(10), pp. 1-6, publ. May 2016 (Year: 2016).*
Bhat et. al., "Rp5063 prevents monocrotaline induced pulmonary arterial hypertension in rats", Am. J. Respir. Crit. Care Med. 193: 2016: A7286, poster session May 18, 2016 (Year: 2016).*
DrugBank Online, "Brilaroxazine", pp. 1-4, publ. Oct. 22, 2015 (Year: 2015).*
King et. al., Lancet, vol. 378, pp. 1949-1961, publ. 2011 (Year: 2011).*
Miller et. al., Amer. J. Respir. Crit. Care Med., vol. 185(11), pp. 1154-1165, publ. Jun. 1, 2012 (Year: 2012).*
Homer et. al., Curr. Opin. Rheumatology, vol. 22, pp. 683-689, publ. 2010 (Year: 2010).*
Miller et. al., Am. J. Respir. Crit. Care Med., vol. 185(11), pp. 1154-1165, publ. 2012 (Year: 2012).
Tawfik et. al., Eur. J. Pharmacology, vol. 814, pp. 114-123, publ. Aug. 16, 2017 (Year: 2017).
Fulton et. al., Int. J. Gen. Med., vol. 8, pp. 309-318, publ. 2015 (Year: 2015).

* cited by examiner

*Primary Examiner* — Sarah Pihonak
(74) *Attorney, Agent, or Firm* — Perkins Coie LLP; Viola T. Kung

(57) ABSTRACT

The present invention provides a method of using arylpiperazine derivatives for treating pulmonary fibrosis. The method comprises a step of administering to a pulmonary fibrosis patient in need thereof an effective amount of a compound of Formula 1, which is an arylpiperazine derivative.

Formula I

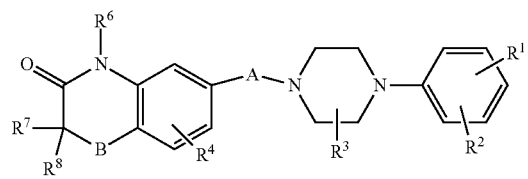

9 Claims, 8 Drawing Sheets

A.

B.

C.

METHODS FOR TREATING PULMONARY FIBROSIS

This application is a continuation of U.S. application Ser. No. 17/143,872, filed Jan. 7, 2021; which is a continuation of U.S. application Ser. No. 16/913,414, filed Jun. 26, 2020; which is a continuation of PCT/US2018/067999, filed Dec. 28, 2018; which claims the benefit of U.S. Provisional Application No. 62/611,501, filed Dec. 28, 2017. The contents of the above-identified applications are incorporated herein by reference in their entirety.

TECHNICAL FIELD

The present invention relates to methods of utilizing arylpiperazine derivatives for treating pulmonary fibrosis.

BACKGROUND

Pulmonary fibrosis (PF) is a progressive respiratory disorder characterized by a scarring and thickening of the lining of the lungs that causes irreversible loss of ability to transport and exchange oxygen. As lung tissue scars, it becomes more rigid, making it more difficult for the lungs to inflate and deflate. When this happens, less oxygen is transferred into the bloodstream, making it harder to breathe. As PF worsens, a person becomes progressively weaker and short of breath, and this damage eventually results in death. When an etiology for PF cannot be clearly identified, the condition is termed idiopathic pulmonary fibrosis (IPF).

IPF, a chronic disease that destroys the small interstitial spaces within the lungs, is the most common type of diffuse parenchymal lung disease. IPF is increasingly understood to be the result of an irreversible fibroproliferative and aberrant wound-healing cascade. The course of pulmonary fibrosis and the severity of symptoms can vary considerably from person to person. The major signs and symptoms of PF include shortness of breath (dyspnea), a dry cough, fatigue, unexplained weight loss, aching muscles and joints, and widening and rounding of the tips of the fingers or toes (clubbing). Co-morbidities are common with individuals with PF. The most commonly associated co-morbidities are emphysema (often clinically termed CPFE: combined pulmonary fibrosis and emphysema), pulmonary hypertension (PH), venous thromboembolism, lung cancer, gastroesophageal reflux disease (GERD), cardiovascular disease, diabetes, and neuropsychiatric symptoms such as psychosis, depression, anxiety, and cognitive deficit.

The precise prevalence of IPF worldwide is unknown, but the American Lung Association estimates that IPF affects about 140,000 Americans yearly, and about 40,000 people die from it each year. IPF typically occurs in people aged≥50 years (range, 40-70 years), and more men than women are affected. Median survival is 2 to 3 years after initial diagnosis. About two-thirds of IPF patients die within 5 years, and the risk of death increases with age.

Although many advances have been made in recent years, especially pertaining to the molecular genetics and cell biology of pulmonary fibrisis (PF), the pathogenesis of PF is still not fully understood. Injuries to epithelial or endothelial cells and disruptions in normal wound healing process contribute to the development of pulmonary fibrosis (Wynn 2011). Alveoli fibrosis, vascular fibrosis, blood clotting and coagulation, lung inflammation and respiratory resistance are morphological hallmarks of pulmonary fibrosis (Wynn 2011). Serotonin (5-HT) and key serotonin receptors have been reported to play a key role in the pathobiology of PF. Eleveated serotonin levels and expression of serotonin $5-HT_{2A}$, $5-HT_{2B}$ and $5-HT_7$ receptors are reported in the epithelial and endothelial cells of PF patients. $5-HT_{2A}$ receptor modulation reported to regulate blood clotting and coagulation, prolifereation and vasorelaxation. $5-HT_{2B}$ receptor modulation is reported to play central role in the regulation of fibrosis and proliferation whereas $5-HT_7$ is receptor reported to regulate inflammatory cytokines and chemokines (Lofdhal 2016, Mann 2013, and Dees 2011).

Despite growing knowledge of the pathobiology of pulmonary fibrosis (PF), the prognosis of patients remains poor. PF is irreversible and currently, there is no therapy to stop or significantly delay the disease progress. Typically, treatment strategies for PF aim to improve quality of life (i.e., relieve disease signs/symptoms) or attempt to limit further inflammation and scarring. Anti-inflammatory drugs, including corticosteroids and cytotoxic agents, are used even though there is no evidence of a benefit for long-term survival. Pirfenidone and nintedanib are the two FDA approved drugs for the management of IPF. Both pirfenidone and nintedanib are reported to reduce fibrotic tissue to some extent in the lungs of patients with pulmonary fibrosis, but the treatment is far from optimal. There is a pressing need for more effective and tolerable next generation therapies or treatments that can significantly delay the progression of pulmonary fibrosis, if not provide a cure and improve patients' overall quality of life (QOL).

DETAILED DESCRIPTION OF THE INVENTION

Definitions

Figure 1:
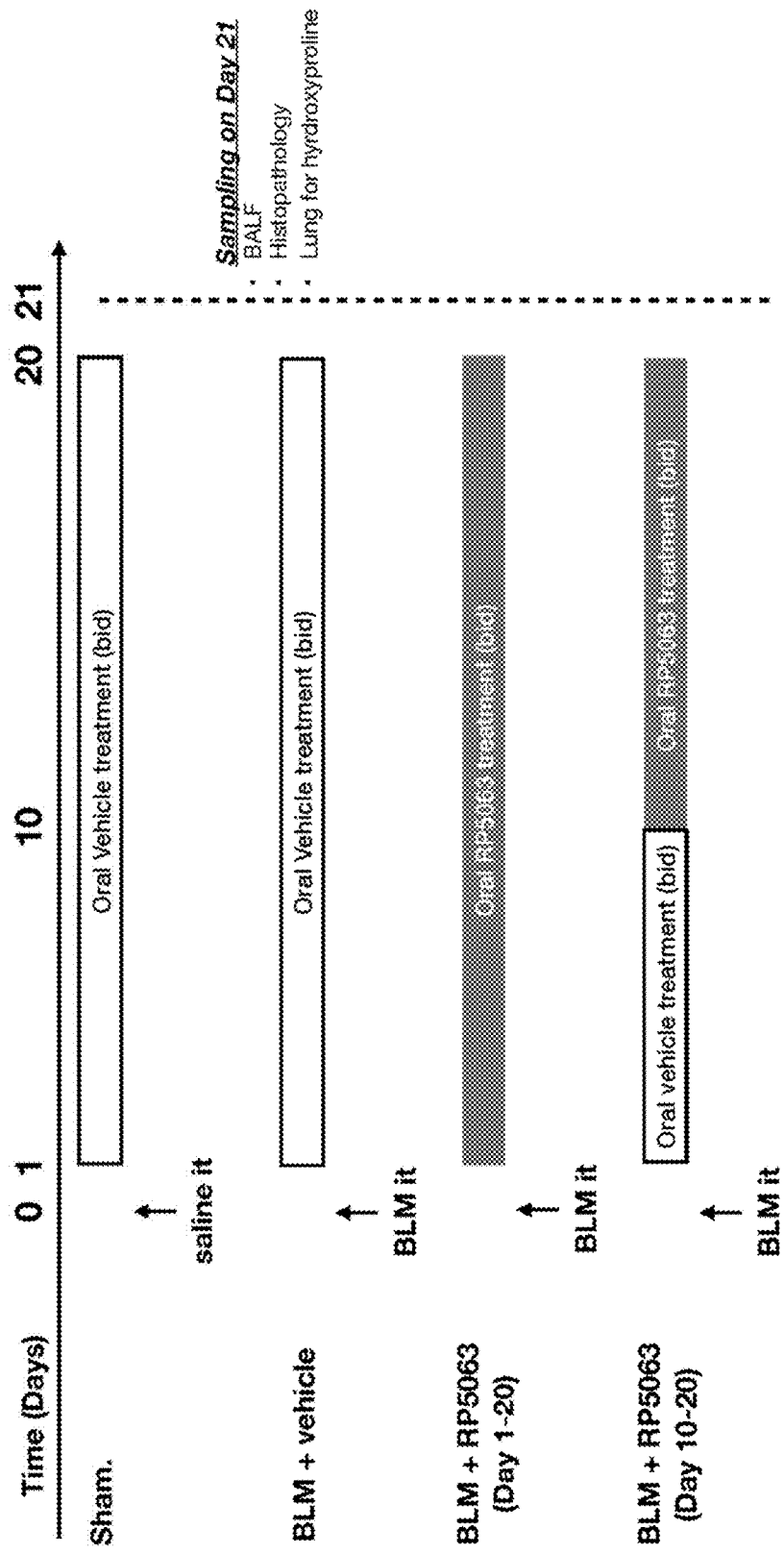
FIG. 1 depicts the schedule of various treatments of the animals during the bleomycin-induced IPF study

"Alkyl" or "alkanyl" refers to a saturated, branched or straight-chain or cyclic monovalent hydrocarbon radical derived by the removal of one hydrogen atom from a single carbon atom of a parent alkane. Typical alkyl groups include, but are not limited to methyl; ethyl; propyls such as propan-1-yl, propan-2yl, cyclopropan-1-yl; butyls such as butan-1-yl, butan-2-yl, 2-methyl-propan-1-yl, 2-methyl-propan-2-yl, cyclobutan-1-yl and the like. Preferably, an alkyl group comprises from 1-20 carbon atoms, more preferably, from 1 to 10, or 1 to 6, or 1-4 carbon atoms.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acylamino" refers to "amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined/herein that may be optionally substituted by one or more substituents as defined herein. Representative examples include, but are not limited to methylthio, ethylthio, propylthio, butylthio, and the like.

"Amide" or "acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonyl-amino, benzoylamino, benzylcarbonylamino and the like.

"Amino" refers to the radical —NH$_2$.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, naphthylmethyl, 2-naphthylethan-1-yl, naphthobenzyl, 2-naphthophenylethan-1-yl and the like. Preferably, an arylalkyl group is (C$_6$-C$_{30}$)arylalkyl, e.g., the alkyl moiety of the arylalkyl group is (C$_1$-C$_{10}$) and the aryl moiety is (C$_6$-C$_{20}$), more preferably, an arylalkyl group is (C$_6$-C$_{20}$) arylalkyl, e.g., the alkyl moiety of the arylalkyl group is (C$_1$-C$_8$) and the aryl moiety is (C$_6$-C$_{12}$).

"Arylalkoxy" refers to an —O-arylalkyl radical where arylalkyl is as defined herein that may be optionally substituted by one or more substituents as defined herein.

"Aryloxycarbonyl" refers to radical —C(O)—O-aryl where aryl is defined herein that may be optionally substituted by one or more substituents as defined herein.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—C(O)OCH$_3$), cyclohexyl carbonate (—C(O)OC$_6$H$_{11}$), phenyl carbonate (—C(O)OC$_6$H$_5$), benzyl carbonate (—C(O)OCH$_2$C$_6$H$_5$), and the like.

"Carboxy" means the radical —C(O)OH.

"Cyano" means the radical —CN.

"Cycloalkyl" refers to a substituted or unsubstituted cylic alkyl radical. Typical cycloalkyl groups include, but are not limited to, groups derived from cyclopropane, cyclobutane, cyclopentane, cyclohexane, and the like. In a preferred embodiment, the cycloalkyl group is (C$_3$-C$_{10}$) cycloalkyl, more preferably (C$_3$-C$_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Halogen" means fluoro, chloro, bromo, or iodo.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Preferably, the heteroarylalkyl radical is a 6-30 carbon membered heteroarylalkyl, e.g., the alkyl moiety of the heteroarylalkyl is 1-10 membered and the heteroaryl moiety is a 5-20 membered heteroaryl, more preferably, a 6-20 membered heteroarylalkyl, e.g., the alkyl moiety of the heteroarylalkyl is 1-8 membered and the heteroaryl moiety is a 5-12 membered heteroaryl.

"Hydroxy" means the radical —OH.

"Oxo" means the divalent radical =O.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Racemate" refers to an equimolar mixture of enantiomers of a chiral molecule.

"Substituted" refers to a group in which one or more hydrogen atoms are each independently replaced with the same or different substituents(s). Typical substituents include, but are not limited to, —X, —R$^{54}$, —O$^-$, =O, —OR$^{54}$, —SR$^{54}$, —S$^-$, =S, —NR$^{54}$R$^{55}$, =NR$^{54}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$OR$^{54}$, —OS(O)$_2$O$^{31}$, —OS(O)$_2$R$^{54}$, —P(O)(O$^-$)$_2$, —P(O)(OR$^{14}$)(O$^{31}$), —OP(O)(OR$^{54}$)(OR$^{55}$), —C(O)R$^{54}$, —C(S)R$^{54}$, —C(O)OR$^{54}$, —C(O)NR$^{54}$R$^{55}$, —C(O)O$^-$, —C(S)OR$^{54}$, —NR$^{56}$C(O)N$^{54}$R$^{55}$, —NR$^{56}$C(S)NR$^{54}$R$^{55}$, —NR$^{57}$C(NR$^{56}$)NR$^{54}$R$^{55}$, and —C(NR$^{56}$)NR$^{54}$R$^{55}$, where each X is independently a halogen; each R$^5$, R$^{55}$, R$^6$ and R$^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{58}$R$^{59}$, —C(O)R$^{58}$ or —S(O)$_2$R$^{58}$ or optionally R$^{58}$ and R$^{59}$ together with the atom to which they are both attached form a cycloheteroalkyl or substituted cycloheteroalkyl ring; and R$^{58}$ and R$^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both.

"Therapeutically effective amount" means the amount of a compound that, when administered to a patient for treating a disease, is sufficient to affect such treatment for the disease. The "therapeutically effective amount" will vary depending on the compound, the disease and is severity and the age, weight, etc., of the patient to be treated, and can be determined by one of skill in the art without undue experimentation.

The present invention is directed to a method for treating pulmonary fibrosis.

Compounds Useful for the Invention

Compounds of Formula (I) are useful for the present invention:

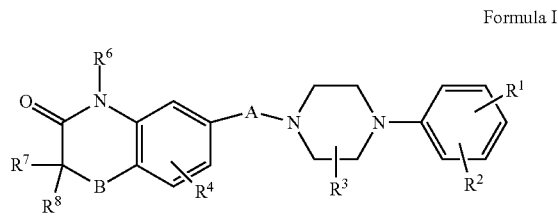

Formula I wherein:

A is —O—(CH$_2$)$_n$—, —(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$))(—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, or (CH$_2$)$_n$—S—C(O)—CH$_2$—CH$_2$—, wherein n is an integer from 1 to 7, preferably n is 2 to 5, for example n is 4;

B is O, S, S(O)(O), or NR$^5$; and each of R$^1$, R$^2$, R$^3$, R$^4$, R$^5$, R$^6$, R$^7$, and R$^8$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide, wherein R$^1$, R$^2$, R$^3$, R$^4$, R$^5$, R$^6$, R$^7$ and R$^8$ and A may optionally be substituted with isotopes that include, but not limited to $^2$H (deuterium), $^3$H (tritium), $^{13}$C, $^{36}$Cl, $^{18}$F, $^{15}$N, $^{17}$O, $^{18}$O, $^{31}$P, $^{32}$P, and $^{35}$S; with $^2$H (deuterium) being preferred;

or a pharmaceutically acceptable salt, racemate or diastereomeric mixtures thereof.

In one aspect of the invention, A is —O—(CH$_2$)$_n$—.

In one aspect of the invention, A is —(CH$_2$)$_n$—.

In another aspect of the invention, A is —S—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, or —(CH$_2$)$_n$—S—CH$_2$—CH$_2$—; with A being —O—(CH$_2$)$_n$— preferred.

In another aspect of the invention, A is —NH—C(O)—(CH$_2$)$_n$—, —CH$_2$—NH—C(O)—(CH$_2$)$_n$—, —CH$_2$—C(O)—NH—(CH$_2$)$_n$— or —(CH$_2$)$_n$—C(O)—NH—CH$_2$—CH$_2$—.

In another aspect of the invention, B is O.

In another aspect of the invention, R$^3$, R$^4$, R$^6$, R$^6$, and R$^8$ are H.

In a preferred embodiment, A is —O—(CH$_2$)$_n$— or —NH—C(O)—(CH$_2$)$_n$—, n=2-5.

In a preferred embodiment, B is O.

In a preferred embodiment, R$^3$, R$^4$, R$^6$, R$^6$, and R$^8$ are H.

In a preferred embodiment, each of R$^1$ and R$^2$ is independently H, halogen (e.g., chloro), haloalkyl, or alkoxy (e.g., methoxy or ethoxy); preferably halogen or alkoxy.

Preferred compounds of Formula I include, for example, the following Compounds A-D and their hydrochloride salt.

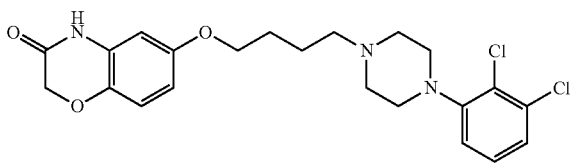 [SMILES: O=C1COc2ccc(OCCCCN3CCN(c4cccc(Cl)c4Cl)CC3)cc2N1]

6-(4-(4-(2,3-dichlorophenyl)piperazin-1-yl)butoxy)-2H-benzo[b][1,4]oxazin-3(4H)-one (brilaroxazine, or Compound A);

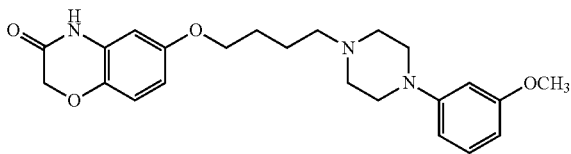 [SMILES: COc1cccc(N2CCN(CCCCOc3ccc4c(c3)NC(=O)CO4)CC2)c1]

6-(4-(4-(2-methoxyphenyl)piperazin-1-yl)butoxy)-2H-benzo[b][1,4]oxazin-3(-4H)-one (Compound B);

(Compound C)

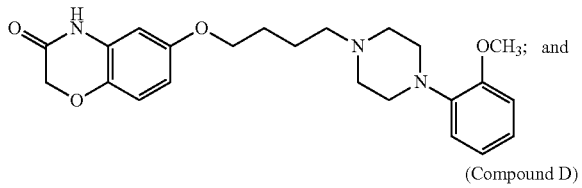

(Compound D)

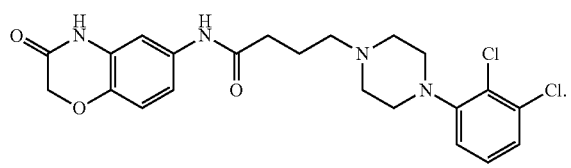

The compounds useful for the present invention further pertain to enantiomerically isolated compounds of Formula I. The isolated enantiomeric forms of the compounds of Formula I are substantially free from one another (i.e., in enantiomeric excess). In other words, the "R" forms of the compounds are substantially free from the "S" forms of the compounds and are, thus, in enantiomeric excess of the "R" forms. Conversely, "S" forms of the compounds are substantially free of "R" forms of the compounds and are, thus, in enantiomeric excess of the "S" forms. In one embodiment of the invention, the isolated enantiomeric compounds are at least about in 80% enantiomeric excess. Thus, for example, the compounds are at least about 90%/enantiomeric excess, preferably at least about 95% enantiomeric excess, more preferably at least about 97% enantiomeric excess, or even more preferably, at least 99% or greater than 99% enantiomeric excess.

Formula I compounds can be synthesized according U.S. Pat. No. 8,188,076, which is incorporated herewith in its entirety.

Method of Treating Pulmonary Fibrosis

The present invention is directed to a method for treating pulmonary fibrosis (PF) and idiopathic pulmonary fibrosis (IPF). When the cause for PF cannot be clearly identified, the condition is termed IPF. Although the cause of PF and IPF may be different, the signs and symptoms of PF and IPF are the same, and the present invention is effective to treat PF and IPF, regardless the cause of the disease. The method comprises the step of administering an effective amount of a compound of Formula I to a patient who is suffering from pulmonary fibrosis. Formula I compounds can lower fibrosis in the pulmonary artery (the blood vessel that leads from the heart to the lungs) or alveoli of a patient and treat pulmonary fibrosis. The treatment can also reduce disease complications, such as lung inflammation, shortness of breath, pain crisis, pneumonia, and increase survival.

In one embodiment, the method treats pulmonary fibrosis in a subject with chronic obstructive pulmonary disease (COPD), with pulmonary arterial hypertension (PAH), with sickle cell disease (SCD), with scleroderma or with lung cancer.

In one embodiment, the method treats comorbid mental illnesses such as psychosis, depression, and mood symptoms in patients with pulmonary fibrosis. In another embodiment, the method treats anxiety in patients with pulmonary fibrosis.

When used to treat pulmonary fibrosis, one or more compound of Formula I can be administered alone, or in combination with other agents, to a patient. The patient may be an animal, preferably a mammal, and more preferably a human.

Formula I compounds are preferably administered orally. Formula I compounds may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin. Inhalation or transdermal administration may be preferred for young children.

Formula I compounds can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In one embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In one embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

Formula I compounds may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Pharmaceutical Formulation of the Invention

The present invention is directed to a pharmaceutical formulation for treating pulmonary fibrosis. The pharmaceutical formulation contains a therapeutically effective amount of one or more compounds of Formula I, preferably in purified form, together with a suitable amount of a pharmaceutically acceptable vehicle. When administered to a patient, the pharmaceutical formulation is preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17$^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcarnitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598;

Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

Dosage for the Treatment

The amount of Formula I compound administered is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In one embodiment, the compounds of the invention are delivered by oral sustained release administration. In one embodiment, the compounds of the invention are administered twice per day, and preferably, once per day. Dosing may be repeated intermittently, may be provided alone or in combination with other drugs, and may continue as long as required for effective treatment of the disease state or disorder.

The compounds of Formula I may be administered in the range 0.1 mg to 500 mg, preferably 1 mg to 100 mg per day, such as 5 mg, 10 mg, 15 mg, 20 mg, 25 mg, 35 mg or 50 mg per day, and preferably 10 mg per day.

Combination Therapy

In certain embodiments of the present invention, the compounds of the invention can be used in combination therapy with at least one other therapeutic agent. Formula I compounds and the therapeutic agent can act additively or synergistically. In one embodiment, Formula I compound is administered concurrently with the administration of another therapeutic agent, which can be part of the same composition of Formula I compound. In another embodiment, a composition comprising a compound of the invention is administered prior or subsequent to administration of another therapeutic agent.

The present invention is effective for treating pulmonary fibrosis. Compounds of Formula I have potent binding affinity at the serotonin 5-$HT_{2A}$ receptor (compound A, Ki=2.5 nM, see Example 1), 5-$HT_{2B}$ receptor (compound A, Ki=0.19 nM, see Example 1), and 5-$HT_7$ receptor (compound A, Ki=2.7 nM, see Example 1). In addition, Compounds of Formula I exhibit partial agonist activities for the key subtypes of dopamine (D2) and serotonin (5-$HT_{1A}$), and antagonist activity at the serotonin 5-$HT_6$ receptors. Furthermore, compounds of Formula I (compound A) demonstrated efficacy for treating pulmonary fibrosis in bleomycin induced pulmonary fibrosis rat model (Example 2).

The invention is illustrated by the following examples.

EXAMPLES

Example 1. In Vitro Pharmacology Results

Two arylpiperazine derivatives of Formula (I), Compound A and Compound B, were tested in the in vitro pharmacological assays to evaluate their activities for dopamine, $D_{2S}$, serotonin, 5-$HT_{1A}$, 5-$HT_{2A}$, 5-$HT_{2B}$, 5-$HT_6$, and 5-$HT_7$ receptors. The in vitro assay protocols and literature references are described herein.

Dopamine, $D_{2S}$ Radioligand Binding Assay

Materials and Methods:
   Receptor Source: Human recombinant $D_{2S}$ expressed mammalian cells
   Radioligand: [$^3$H]Spiperone (20-60 Ci/mmol) or [3H]-7-hydroxy DPAT, 1.0 nM
   Control Compound: Haloperidol or Chlorpromazine
   Incubation Conditions: The reactions were carried out in 50 mM TRIS-HCl (pH 7.4) containing 120 mM NaCl, 5 mM KCl, 5 mM $MgCl_2$, 1 mM EDTA for 60 minutes at 25 C. The reaction was terminated by rapid vacuum filtration onto glass fiber filters. Radioactivity trapped onto the filters was determined and compared to control values in order to ascertain any interactions of test compounds with the cloned dopamine-$D_2$ short binding site (Literature Reference: Jarvis, K. R. et al. Journal of Receptor Research 1993, 13(1-4), 573-590; Gundlach, A. L. et al. Life Sciences 1984, 35, 1981-1988.)

Serotonin, 5$HT_{1A}$ Radioligand Binding Assay

Materials and Methods:
   Receptor Source: Human recombinant 5-$HT_{1A}$ expressed mammalian cells
   Radioligand: [$^3$H]-8-OH-DPAT (221 Ci/mmol)
   Control Compound: 8-OH-DPAT
   Incubation Conditions: The reactions were carried out in 50 mM TRIS-HCl (pH 7.4) containing 10 mM $MgSO_4$, 0.5 mM EDTA and 0.1% Ascorbic acid at room temperature for 1 hour. The reaction was terminated by rapid vacuum filtration onto glass fiber filters. Radioactivity trapped onto the filters was determined and compared to control values in order to ascertain any interactions of test compounds with the cloned serotonin-5$HT_{1A}$ binding site (Literature Reference: Hoyer, D. et al. Eur. Journal Pharmacol. 1985, 118, 13-23; Schoeffler, P. and Hoyer, D. Naunyn-Schmiedeberg's Arch. Pharmac. 1989, 340, 135-138)

Serotonin, 5$HT_{2A}$ Radioligand Binding Assay

Materials and Methods:
   Receptor Source: Human Cortex or Human recombinant 5-$HT_{2A}$ expressed mammalian cells
   Radioligand: [$^3$H]-Ketanserin (60-90 Ci/mmol)
   Control Compound: Ketanserin
   Incubation Conditions: The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin-5$HT_{2A}$ binding site (Literature Reference: Leysen, J. E. et al. Mol. Pharmacol. 1982, 21, 301-314; Martin, G. R. and Humphrey, P. P. A. Neuropharmacol. 1994, 33(3/4), 261-273.)

Serotonin, 5$HT_{2B}$ Radioligand Binding Assay

Materials and Methods:
   Receptor Source: Human recombinant 5-$HT_{2B}$ expressed CHO-K1 cells
   Radioligand: 1.20 nM [3H] Lysergic acid diethylamide (LSD)
   Control Compound: Ketanserin
   Incubation Conditions: The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin-$5HT_{2B}$ binding site.

Serotonin, $5HT_6$ Radioligand Binding Assay

Materials and Methods:

Receptor Source: Human recombinant $5\text{-}HT_6$ expressed mammalian cells

Radioligand: [125I] SB258585, 15 nM or [$^3$H]LSD, 2 nM

Control Compound: Methiothepin or serotonin

Incubation Conditions: The reactions were carried out in 50 mM TRIS-HCl (pH 7.4) containing 10 mM $MgSO_4$, 0.5 mM EDTA and 0.1% Ascorbic acid at room temperature for 1 hour. The reaction was terminated by rapid vacuum filtration onto glass fiber filters. Radioactivity trapped onto the filters was determined and compared to control values in order to ascertain any interactions of test compounds with the cloned serotonin-$5HT_6$ binding site (Literature Reference: Gonzalo, R., et al., Br. J. Pharmacol., 2006 (148), 1133-1143).

Serotonin, $5HT_7$ Radioligand Binding Assay

Materials and Methods:

Receptor Source: Human recombinant $5\text{-}HT_7$ expressed CHO cells

Radioligand: [3H] Lysergic acid diethylamide (LSD), 4 nM

Control Compound: Serotonin

Incubation Conditions: The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin-$5HT_7$ binding site The radioligand binding assays were carried out at six to 10 different concentrations and the test concentrations were 0.1 nM, 0.3 nM, 1 nM, 10 nm, 30 nM, 100 nM, 300 nM and 1000 nM.

The in vitro pharmacological activities of the selected compounds A and B using radioligand binding assays are reported in the following table. Compound A (brilaroxazine) =6-(4-(4-(2,3-dichlorophenyl)piperazin-1-yl)butoxy)-2H-benzo[b][1,4]oxazin-3(4H)-one hydrochloride. Compound B=6-(4-(4-(2-methoxyphenyl)piperazin-1-yl)butoxy)-2H-benzo[b][1,4]oxazin-3(-4H)-one hydrochloride.

| Compound | Assay | Ki |
|---|---|---|
| A | D2S | 0.62 nM |
| A | 5-HT1A | 1.50 nM |
| A | 5-HT2A | 2.50 nM |
| A | 5-HT2B | 0.19 nM |
| A | 5-HT6 | 51 nM |
| A | 5-HT7 | 2.70 nM |
| B | D2S | 0.30 nM |
| B | 5-HT1A | 0.65 nM |
| B | 5-HT2A | 118 nM |

Example 2. Evaluation of the Effects of Compound a (RP5063) in the Bleomycin (BLM) Induced Pulmonary Fibrosis Rat Model Materials and Methods Study Animals: The investigation involved 34 male Sprague Dawley rats (weights: 275-300 g; ages: 8 weeks; Charles River Laboratories, Quebec, Canada) randomized for equal distribution according to their body weight into four groups. Study Design: The objective of this parallel-design study was to evaluate the effectiveness of Compound A (RP5063) started on Day 1 and on Day 10 following BLM-induction on the functional, histologic, and patho-physiologic parameters in the BLM-induced model.

Study Methods: On Day 0, animals in Group 1 (Sham; N=5) received one intratracheal administration of the vehicle, 0.250 mL of vehicle 0.9% saline solution (FIG. 1). Animals in Groups 2 to 4 (n=9, 10, 10, respectively) received a single intratracheal instillation of 0.250 mL (5 U/kg-3.33 mg/kg) of bleomycin sulfate (Cayman Chemicals, Ann Arbor, MI) solution. From Day 1 to 10, the vehicle was administered to Groups 1, 2, and 4. Compound A (RP5063) 15 mg/kg per gavage twice-daily (b.i.d.) was administered to Group 3 as treatment from Day 1 to 20 (Group 3, RPT). The vehicle administration was continued to Group 1 (Sham) and Group 2 (BLM) until Day 20. From Day 10 to 20, the Group 4 received 15 mg/kg per gavage twice-daily (b.i.d.) Compound A (RP5063) as an intervention treatment (Group 4, RPI). During the treatment period, food and water were provided ad libitum to the rats. On each day, animals were monitored for behavior, general health status, and survival. Body weight and food intake were also measured.

The solution used was prepared by dissolving 750 mg of Compound A (RP5063) in 500 mL of sterile 5% glucose solution to obtain a solution of 1.5 mg/mL. For bleomycin, 50 mg of drug was weighed and dissolved in 12.5 mL of sterile 0.9% Saline solution was added to obtain a solution of 4 mg/mL. The vehicle was created by dissolving 50 g of glucose in 1 L of water to result in a 5% solution.

On Day 21, animals were anesthetized and instrumented. Hemodynamic parameters (systemic arterial blood pressure, heart rate, and oxygen saturation) were recorded continuously for at least 5 minutes. At the end of the recording, a blood sample was collected. After the animal was exsanguinated, the pulmonary circulation was flushed with 0.9% NaCl, and tissues (lungs, trachea, and heart) were harvested altogether from the thoracic cavity for further analysis.

Parameters Measured on Surgery Day: Cardiac activity was recorded continuously during the surgical procedure. Cardiac activity was monitored using three electrocardiographic (ECG) contact electrodes placed in a lead-I/II configuration and connected to an IsoDam8 differential amplifier. Heart rate (HR) was recorded using duplicate systems: from the ECG records (RR-intervals) and using an N-595 pulse oximeter attached to the left front paw of the animal. The heart rate values derived from the pulse oximeter were measured in beat per minutes (bpm) using cursor readings in Clampfit 10.2.0.14CA. Blood oxygen saturation ($SpO_2$) was measured using a pulse oximeter signal attached to the left front paw of the animal.

Systemic arterial blood pressure (SAP) was monitored continuously using an intra-arterial fluid-filled catheter connected to a pressure transducer, with diastolic and systolic pressures values measured in mm Hg. Calculation of mean SAP (mSAP) and pulse pressure (PP) used the following formulas: 1–mSAP=diastolic systemic pressure+([systolic systemic pressure–diastolic systemic pressure]/3); and 2–PP=systolic systemic pressure–diastolic systemic pressure. Pulse pressure was calculated as the difference between systolic and diastolic readings.

After being harvested, the trachea was connected to the cannula of a perfusion system. The left lung was clamped while 5 mL of cold PBS solution was injected in the trachea to perform bronchoalveolar lavage to obtain fluid (BALF) of the right lobe of the lungs and was collected for further analysis (Total cell counts and cytokines measurement). Once the BALF sample was collected, it was centrifuged at 1200 rpm for 10 minutes at 4° C. The supernatant was frozen at −80° C. until cytokines analysis. The cells were then resuspended in PBS and counted with a hemocytometer.

Organ weights were expressed as relative percentages and were calculated as follows: Relative organ weight=(organ weight×100)/body weight.

Histological Preparation and Categorization: For each rat, the left lobe of the lungs was harvested, perfused and fixed with 10% neutral buffered formalin. A transversal section of the middle left lobe was cut and forwarded in 10% NBF to the Institute for Research in Immunology and Cancer (Montreal, Quebec, Canada). Tissues were embedded, sliced (5-μm thickness), mounted, and conventionally stained. Staining included hematoxylin and eosin (H&E) and Ashcroft score and finally, a Masson's trichrome staining for the fibrosis quantification. Glass slides containing fixed and stained tissues were visualized at 20× magnification (Eclipse T100 microscope, Nikon). At least five non-overlapping view fields/lung were selected for microphotographs (Nikon DS-Fi1 digital camera with Nikon NIS Elements 4.30, Nikon).

Alveolar septa and lung structure were estimated using the H&E slides. Tissue was scored with a modified Ashcroft Scale accordingly to the means of the five non-overlapping view fields previously selected. Glass slide tissue stained with Masson's Trichrome was also visualized using a scanner to determine the percentage of the fibrotic tissue on the slice.

Hydroxyproline Determination: Hydroxyproline (a biomarker for PF) content was determined using a colorimetric assay kit (Cell Biolabs Inc, CA, USA). Part of the right lobe was removed and homogenized in 0.1 mL of water. The supernatant was hydrolyzed in 0.1 mL of 10 N HCl for 6 hours at 120° C. Following the addition of 5 mg of activated charcoal, the samples were centrifuged at 10,000 rpm for five minutes, and the supernatant was transferred to a new tube and processed according to the assay's instructions. The absorbance was measured at 540 nm, and the amount of hydroxyproline was determined and corrected for protein content.

Cytokine Quantification: On Day 21, BALF samples were collected immediately following exsanguination of the animal. For all groups, one-half of each sample was saved for analysis of the following cytokines: (1) Macrophage inflammatory protein 1 (MIP1); (2) Monocyte chemoattractant protein 1 (MCP1); (3) Interleukin (IL)-6; (4) Interferon gamma-induced protein 10 (IP10); and (5) RANTES. The cytokine analysis was performed using a Luminex assay (Eve Technologies, Calgary, Alberta).

Analysis and Statistics: The primary outcomes involved survival and weight. Additional parameters of note included cardiopulmonary and pressure parameters at surgery, tissue weights, histologic samples, bronchoalveolar pulmonary lavage fluid cell counts, hydroxyproline levels, and cytokine. Results are expressed as means f SEM. Comparisons were made on normally distributed data using ANOVA, followed by a Fisher post hoc test to assess the difference between BLM group with Graph Pad Prism Software version 7.0 for Mac (San Diego, CA, USA). Comparisons included Sham versus BLM and treatment(s) versus BLM. Treatment differences were not compared. Differences were statistically significant when P values were less than 0.05.

Results

Figure 2:
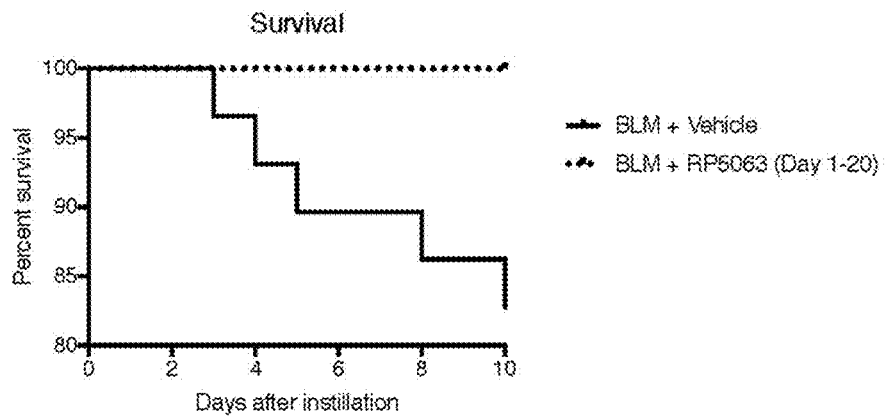
FIG. 2 shows the survival curves from Day 1-10 (A) and from Day 11-21 (B), and body weights (C) of Sham, BLM-induced, and treatment group animals. BLM: Bleomycin; Sham: Non-induced animals with the vehicle. *$P<0.05$ BLM+Veh; as compared to Sham. **$P<0.05$; as compared to BLM+Veh.
Figure 2:
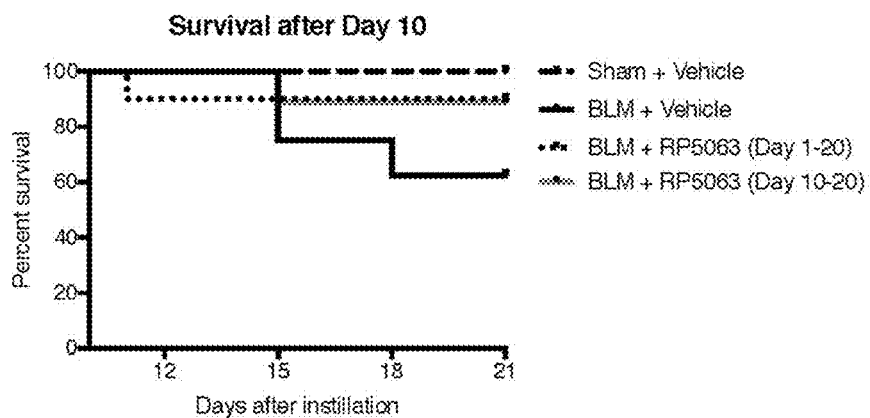
Figure 2:
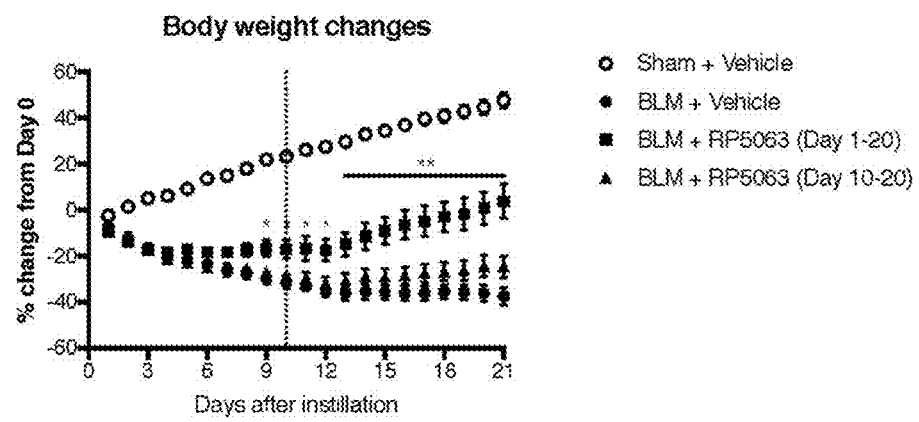

Animal Survival and Weights: Of the 19 animals in Groups 2 and 4, the survival rate at Day 10 was 82% during this period ((P<0.05, Sham). In contrast, the survival rate in non-induced and interventional therapy (RPI) animals (Group 1 and Group 3, respectively) was 100% (P<0.05, BLM) (FIG. 2A). At Day 21, the survival rate for the BLM (Group 2) dropped to 62% (P<0.05, Sham), whereas preventive treatment (RPT) and RPI survival rates were 90% and 89.5% (P<0.05, BLM), respectively (FIG. 2B). Animals in the Sham group continued at 100%.

Mirroring the survival rates were those of body weight (FIG. 2C). Three weeks after BLM induction, the body weight of those in the Sham group increased by approximately 50%; however, the rats in the BLM group was significantly lower (P<0.05, Sham). RPT significantly alleviated BLM-induced weight loss by Day 21 (P<0.01, BLM), as compared with the BLM group. RPT administered from Day 10 following the BLM induction, slightly increased body weight, as compared to BLM-treated rats at Day 21.

Figure 3:
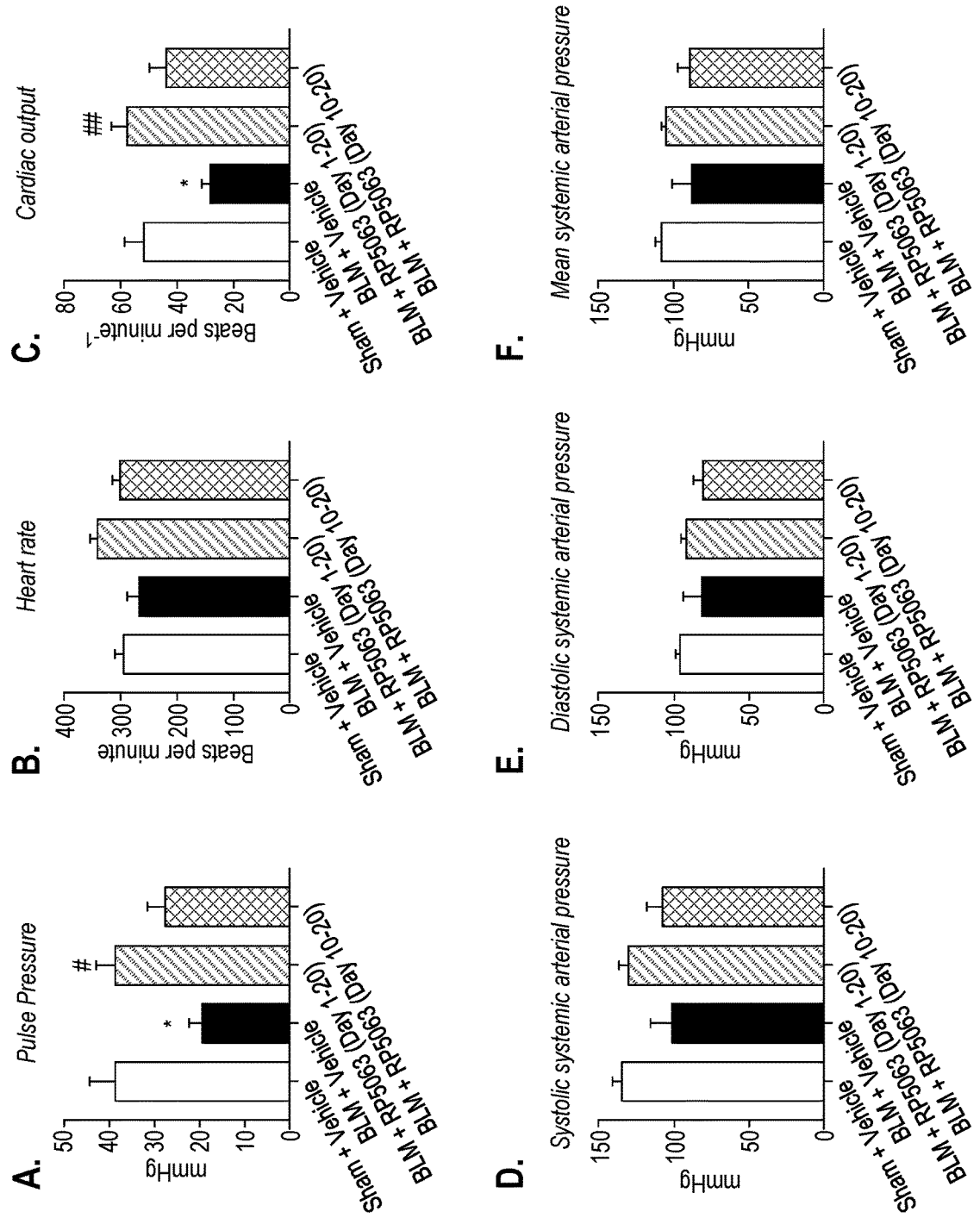
FIG. 3 shows hemodynamic and cardiac parameters (A-C) and systemic arterial pressures (D-F) measured on Day 21. BLM: Bleomycin; Sham: Non-induced animals with the vehicle. *$P<0.05$ BLM+Veh; as compared to Sham. #$P<0.05$; as compared to BLM+Veh. ##$P<0.05$; as compared to BLM+Veh.

Hemodynamic and Cardiac Effects: Hemodynamic parameters were recorded on Day 21 (FIG. 3). Animals in the BLM experienced a significant effect (P<0.05, Sham) of the arterial pulse pressure (FIG. 3A) and cardiac output (FIG. 2B). Ventricular dysfunction (insufficient left ventricular preload) and hypovolemia might account for these observations with pulse pressure. Animals in the RPT experienced an improved arterial pulse pressure (P<0.05, BLM), and were at a similar level that was experienced by those in the Sham group. Additionally, these animals had restored cardiac output, as compared with those on BLM (P<0.01). RPI slightly restored the arterial pulse pressure and cardiac output. Heart rate was relatively similar in all groups (FIG. 3C).

Concerning the systemic arterial pressure (FIG. 3 D-F), while no differences were noted among the groups, animals in the BLM group displayed a non-significant reduction of systemic arterial pressure; this effect was probably a consequence of the cardiac output reduction.

Figure 4:
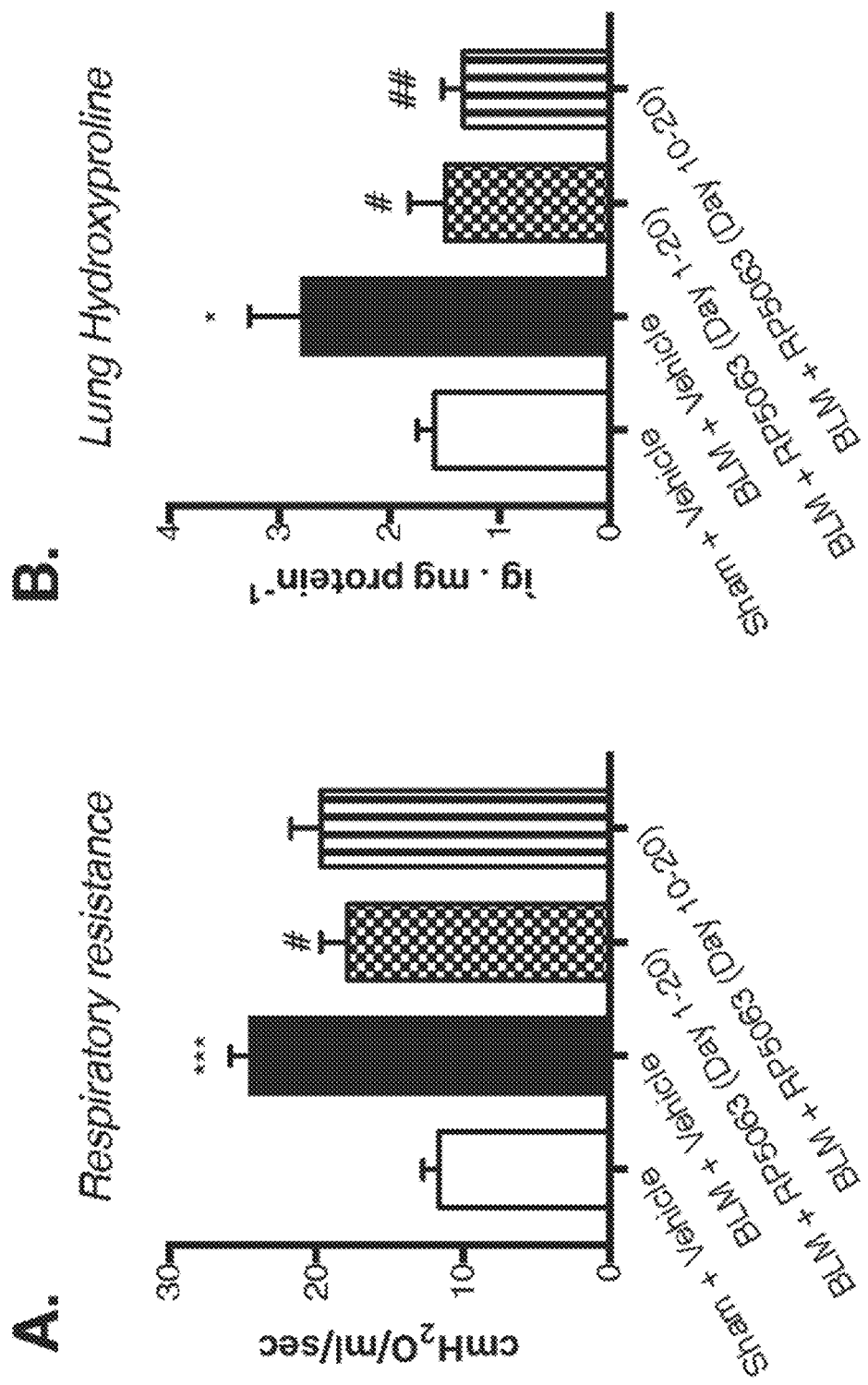
FIG. 4 shows respiratory resistance (A) and lung hydroxyproline (B) measured on Day 21. BLM: Bleomycin; Sham: Non-induced animals with the vehicle. *$P<0.05$, BLM+Veh; as compared to Sham. ***$P<0.001$; as compared to Sham. #$P<0.05$; as compared to BLM+Veh. ##$P<0.01$; as compared to BLM+Veh.

Parameters Reflective of Pulmonary Fibrosis and Function: Pulmonary fibrosis is known to induce respiratory resistance; resistance to the air flow through the respiratory tract during inhalation and exhalation. This resistance reduces gas exchange ($O_2$—$CO_2$) in the alveolar and contributes to reducing lifespan. The BLM animals showed a significant (P<0.001, Sham) increase in respiratory resistance (FIG. 4A). Animals in the RPT group displayed a significant reduction in this parameter (P<0.05, BLM), while those in the RPI group showed improvement (P=0.10, BLM). The hydroxyproline content in the lung was also measured to evaluate the presence of pulmonary fibrosis (FIG. 4B) and reflected changes seen in respiratory resistance. The BLM animals had a two-fold higher hydroxyproline concentration (P<0.05, Sham). Those in the RPT (P<0.05, BLM) and RPI (P<0.01, BLM) groups had a significant diminution in hydroxyproline concentration.

Figure 5:
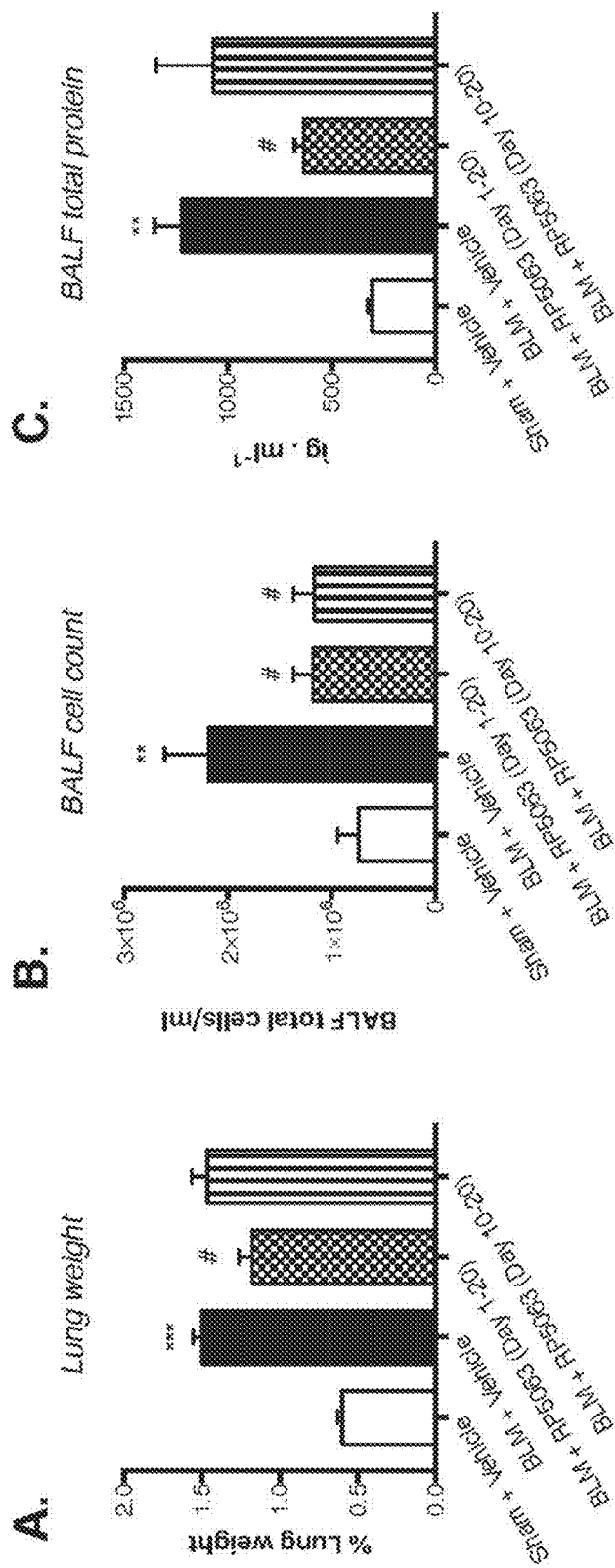
FIG. 5 shows parameters reflective of pulmonary edema at Day 21 including lung weight (A), BALF cell count (B), and BALF total protein (C). BALF: Bronchoalveolar lavage; BLM: Bleomycin; Sham: Non-induced animals with the vehicle. $P<0.01$, BLM+Veh; as compared to Sham. *$P<0.001$; as compared to Sham. #$P<0.05$; as compared to BLM+Veh.

Reflective of the pulmonary changes induced by BLM, animals in the BLM group had significantly (P<0.01, Sham) higher lung weights (FIG. 5A), suggesting the presence of edema. Lung weight of the RPT animals was significantly lower (P<0.05, BLM). The lung weight was also decreased in the RPI group.

Total cell count (inflammation, FIG. 5B) and total protein content (edema, FIG. 5C) were obtained from BALF of the right lobe of the lungs to reinforce lung weight measurements and reflect the presence of pulmonary edema. Both cell counts and protein levels in the BLM animals showed a significant increase (P<0.01, Sham). Animals in the RPT group showed a reversal in both cell counts and protein levels (both, P<0.05, BLM). Animals RPI group significantly reduced the total cell counts (P<0.05, BLM) and showed numerical improvement reduction of BALF protein concentration.

Figure 6:
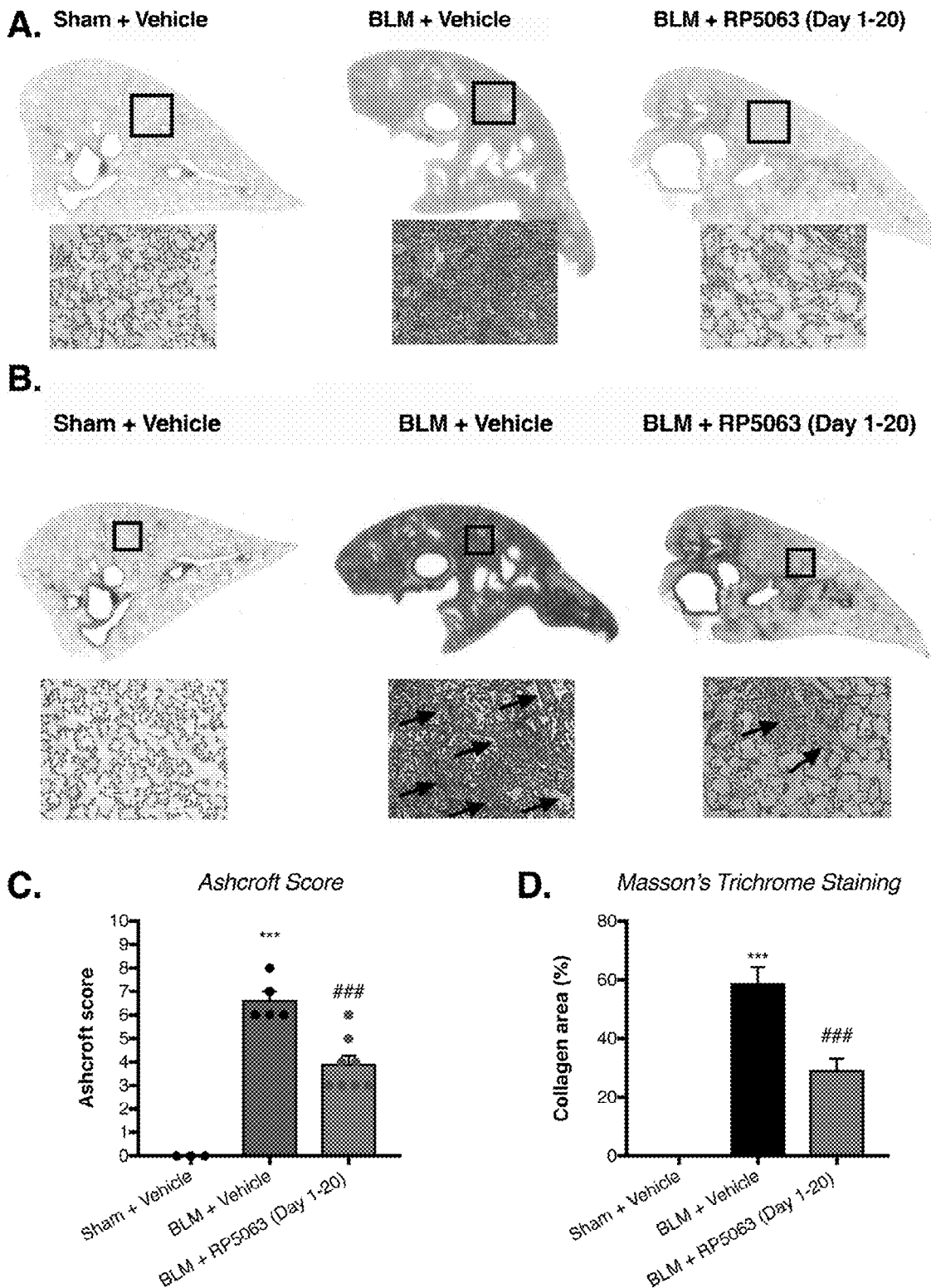
FIG. 6 shows morphology changes displayed by H&E staining and Ashcroft Score (A, C). The collagen deposition is reflected by Masson's trichrome staining (B, D) induced by BLM in rats on Day 21. BLM: Bleomycin; Sham: Non-induced animals with the vehicle. BLM+RP5063 (all animals). ***$P<0.001$; as compared to Sham. ###$P<0.001$; as compared to BLM+Veh.

Staining of lung tissue provided additional evidence reflective of the development of pulmonary fibrosis with BLM and attenuation with RP5063 treatment. As reflected in H&E staining (FIG. 6), the Ashcroft Score in the BLM group lung tissue samples (FIG. 6 A, C) was significant (P<0.001, Sham). Of the treatments, the samples obtained from RPT animals displayed a significant reduction in these lung parenchymal fibrotic changes (FIG. 6C), (P<0.001, BLM). Pulmonary fibrosis is characterized by excessive collagen disposition in the lung, as reflected by percent collagen areas measured with Masson's trichrome staining. Staining samples from animals in the BLM showed a significant (P<0.001, Sham) increase in the percentage of collagen disposition in the lung on Day 21 (FIG. 6 B, D). Therapeutic intervention with RP5063 (RPT) significantly reduced these changes (P<0.001, BLM). These results correlate nicely with the previously presented hydroxyproline concentration quantification.

Figure 7:
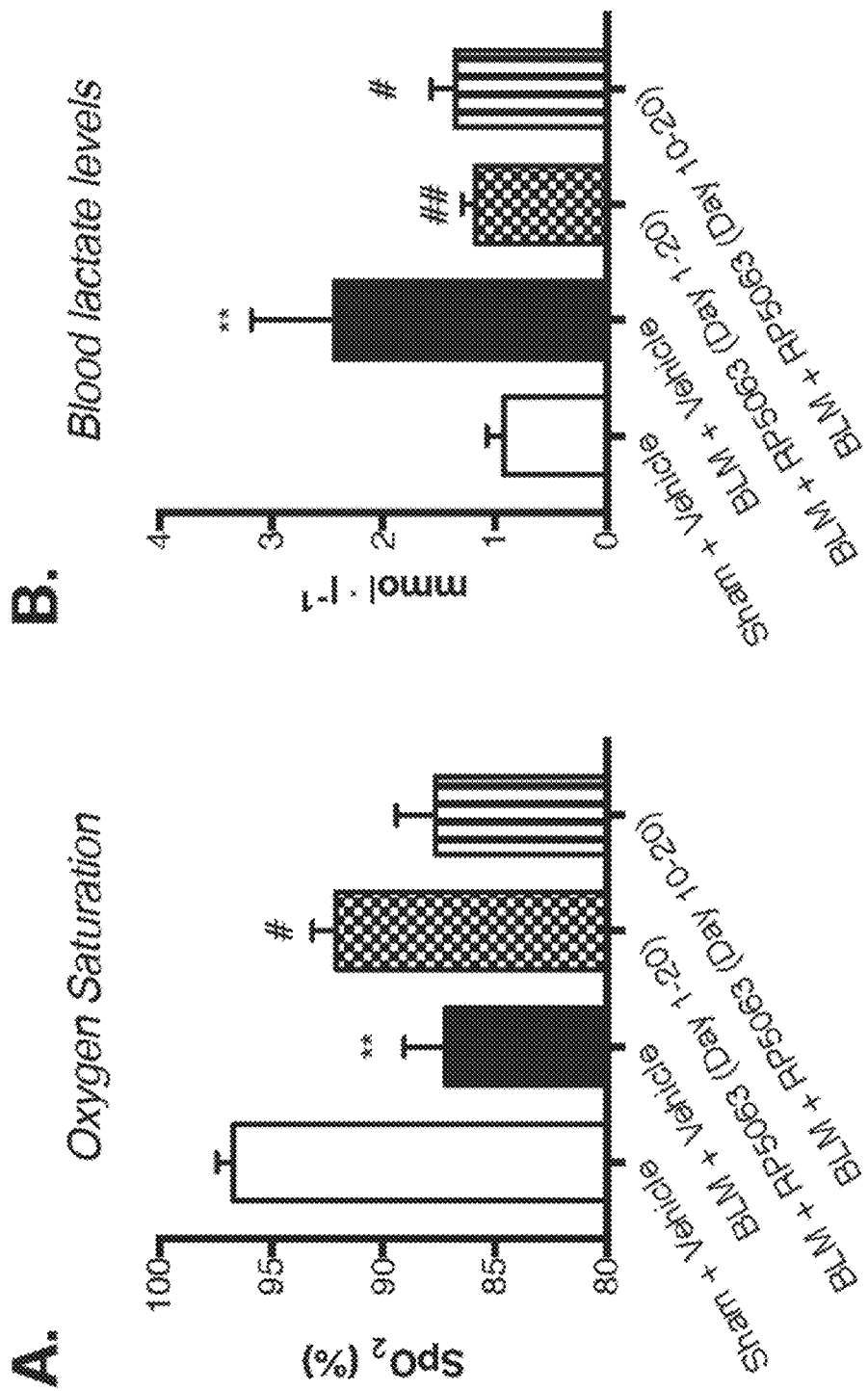
FIG. 7 shows BLM-induced effects on blood oxygen saturation (A) and blood lactate levels (B) measured at Day 21. BLM: Bleomycin; Sham: Non-induced animals with the vehicle. **P<0.01; as compared to Sham. #P<0.05; as compared to BLM+Veh. ##P<0.01; as compared to BLM+Veh.

Reflective of BLM-induced effects on cardiopulmonary capacity, blood oxygen saturation (FIG. 7A) and blood lactate levels (FIG. 7B) were measured at Day 21. The BLM animals showed a significant decrease in saturation and a significant increase in blood lactate levels (both; P<0.01, Sham). Animals in the RPT group showed normalization of the blood oxygen levels (P<0.05, BLM). The saturation levels in RPI animals improved and were numerically better than those the BLM group. While the treatments induced a diminution of blood lactate (a biomarker for PF) levels, both the RPT and RPI were significant (P<0.01, P<0.05, respectively, versus BLM).

Figure 8:
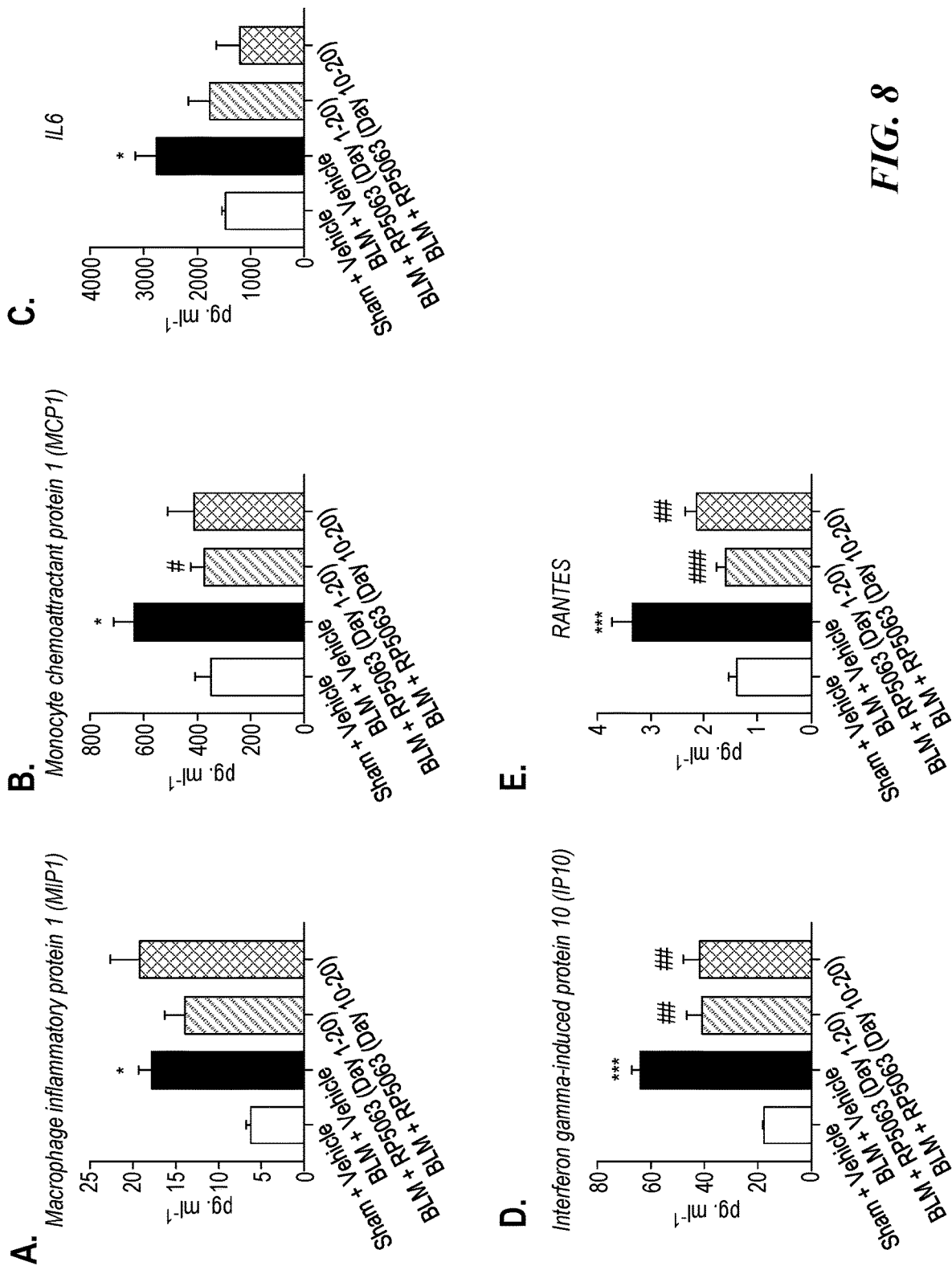
FIG. 8 shows BALF cytokines levels on Day 21: MIP1 (A); MCP1 (B); IL6 (C); IP10 (D); and RANTES (E). BLM: Bleomycin; Sham: Non-induced animals with the vehicle. * P<0.05; as compared to Sham. ***P<0.001; as compared to Sham. #P<0.05; as compared to BLM+Veh. ##P<0.01; as compared to BLM+Veh. ###P<0.001; as compared to BLM+Veh.

BLM-Induced Inflammatory and Fibrogenic Cytokines: To evaluate the impact of treatment on BLM-induced inflammatory and fibrogenic cytokines, analysis of BALF from Day 21 quantified levels of MIP1, MCP1, IL-6, IP10, and RANTES (FIG. 8A-E). Animals in the BLM group displayed a significant increase in all the five cytokines levels (P<0.05 for MIP1 and MCP1; P<0.01 for IP10 and RANTES, Sham). None of the treatments statistically reversed the production of MIP-1 (FIG. 8A), though RPT slightly reduced the production of this cytokine. RP5063 treated animal groups showed reductions in MCP-1 concentrations (FIG. 8B) and those in the RPI group showed a significant decrease (P<0.05, BLM). Animals in both treatment groups had numerically (RPT, RPI) reduced IL6 levels (FIG. 8C). Animals in both RPT and RPI groups showed significant reductions in IP10 (FIG. 8D) (P<0.01, BLM). Finally, animals in both RP5063 treated animals had significantly reduced RANTES cytokine levels (FIG. 8E) (P<0.01, BLM).

CONCLUSIONS

In light of the actual criteria for the demonstration of efficacy for IPF treatment, RP5063 (Compound A, brilaroxazine) was able to significantly affect all important biomarkers and actual endpoints illustrated in the present study. Treatment with RP5063 attenuated BLM-induced pulmonary fibrosis, inflammation, and ECM deposition (collagen) and improved cardiac and pulmonary functions in rodents. RP5063, both as a preventive treatment starting Day 1 (RPT) and as interventional therapy (RPI) beginning on Day 10 following BLM-induction, was able to reduce IPF progression. Positive effects on body weight, survival, lung edema, fibrogenic cytokine production, hydroxyproline content, and respiratory resistance, and cardiopulmonary capacity provide supportive evidence that RP5063 impacts both the functional and pathologic effects associated with IPF. The overall effect in this translational animal model is indicative that RP5063 is an efficacious therapy for the treatment of IPF and PF.

It is to be understood that the foregoing describes preferred embodiments of the present invention and that modifications may be made therein without departing from the scope of the present invention as set forth in the claims.

What is claimed is:

1. A method of treating idiopathic pulmonary fibrosis in a subject, the method comprising administering to a subject suffering from idiopathic pulmonary fibrosis an effective amount of a compound having the following formula,

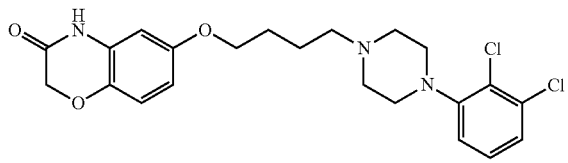 [SMILES: O=C1COc2ccc(OCCCCN3CCN(c4cccc(Cl)c4Cl)CC3)cc2N1]

or a pharmaceutically acceptable salt, racemate, or diastereomeric mixture thereof, whereby the compound lowers alveoli fibrosis and reduces respiratory resistance of the patient.

2. The method according to claim 1, wherein the compound is in a form of a hydrochloride salt.

3. The method according to claim 1, wherein one or more hydrogens of the compound are optionally substituted with $^2$H (deuterium).

4. The method according to claim 1, wherein the compound is administered in a pharmaceutical composition comprising a pharmaceutically acceptable carrier, excipient, or diluent.

5. The method according to claim 1, wherein the compound is orally administered.

6. The method according to claim 1, wherein the method increases blood oxygen, improves cardiac output, and/or increases survival rate.

7. A method of treating pulmonary fibrosis in a subject having chronic obstructive pulmonary disease (COPD), sickle cell anemia, scleroderma, or lung cancer, the method comprising administering to the subject an effective amount of a compound having the following formula,

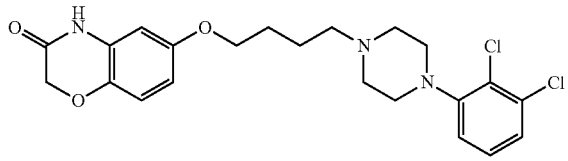 [SMILES: O=C1COc2ccc(OCCCCN3CCN(c4cccc(Cl)c4Cl)CC3)cc2N1]

or a pharmaceutically acceptable salt, racemate, or diastereomeric mixture thereof, whereby the compound lowers alveoli fibrosis and reduces respiratory resistance of the patient.

8. The method of claim 7, wherein said subject has COPD.

9. The method of claim 7, wherein said subject has scleroderma.

* * * * *